United States Patent [19]
Pfeiffer

[11] 4,285,938

[45] Aug. 25, 1981

[54] 7,8-DIHYDROXY-1-(SULFAMYLPHENYL)-2,3,4,5-TETRAHYDRO-1H-3-BENZAZEPINE DERIVATIVES

[75] Inventor: Francis R. Pfeiffer, Cinnaminson, N.J.

[73] Assignee: SmithKline Corporation, Philadelphia, Pa.

[21] Appl. No.: 83,874

[22] Filed: Oct. 11, 1979

[51] Int. Cl.$^3$ .................. A61K 31/33; A61K 31/36; A61K 31/335; C07D 223/16

[52] U.S. Cl. .................. 424/244; 260/239 BB; 260/340.3; 260/340.5 R; 424/278; 424/282

[58] Field of Search .................. 260/239 BB, 340.5 R, 260/340.5, 340.3; 424/278, 282, 244

[56] References Cited

U.S. PATENT DOCUMENTS

| | | | |
|---|---|---|---|
| 3,496,166 | 2/1970 | Mall et al. | 260/239 BB |
| 3,906,006 | 9/1975 | Brossi et al. | 260/239 BB |
| 4,104,379 | 8/1978 | Gallagher, Jr. et al. | 260/239 BB |
| 4,160,765 | 7/1979 | Weinstock | 260/239 BB |
| 4,160,766 | 7/1979 | Bream | 260/239 BB |
| 4,171,359 | 10/1979 | Weinstock | 260/239 BB X |

FOREIGN PATENT DOCUMENTS 555831 11/1974 Switzerland .

*Primary Examiner*—Ethel G. Love
*Attorney, Agent, or Firm*—William H. Edgerton; Richard D. Foggio; Alan D. Lourie

[57] ABSTRACT

New 7,8-dihydroxy-1-(sulfamylphenyl)-2,3,4,5-tetrahydro-1H-3-benzazepines having pharmaceutical activity together with new intermediates and methods of synthesis for preparing them. The lead compound is 6-chloro-7,8-dihydroxy-1-(p-sulfamylphenyl)-2,3,4,5-tetrahydro-1H-3-benzazepine which has very potent renal dopaminergic activity.

17 Claims, No Drawings

7,8-DIHYDROXY-1-(SULFAMYLPHENYL)-2,3,4,5-TETRAHYDRO-1H-3-BENZAZEPINE DERIVATIVES

This invention comprises a new group of 1-phenyl-2,3,4,5-tetrahydro-1H-3-benzazepines whose structures are characterized by having a sulfamyl group (—SO₂NH₂) present on the phenyl ring together with intermediates and chemical processes for preparing them. The end products have pharmaceutical activity especially as dopaminergic agents.

DESCRIPTION OF THE ART

Very few 1-phenyl-2,3,4,5-tetrahydro-1H-3-benzazepines whose structures have a thio containing phenyl substituent are known in the art. U.S. Pat. No. 4,104,379 describes a series of such benzazepine structures which have a lower alkyl thio, lower alkyl sulfonyl, lower alkyl sulfinyl or dimethylsulfonium halide substituent on the 1-phenyl ring. U.S. Pat. No. 3,496,166 discloses, among a large generic group, benzazepine structures having 1-(methylthio or ethylthiophenyl) substitutents. As far as I am aware there are no disclosures in the art of either 1-phenyl-2,3,4,5-tetrahydro-1H-3-benzazepines with a sulfamyl substituent on the 1-phenyl group or a synthetic method readily available for preparing them.

DESCRIPTION OF THE INVENTION

This invention comprises compounds of the following structural formula together with chemical methods and intermediates for preparing them:

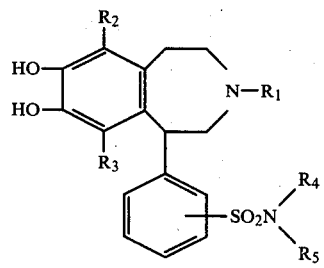

I in which:
- $R_1$ is hydrogen, allyl or lower alkyl such as methyl or ethyl;
- $R_2$ is hydrogen, halo such as chloro, bromo, fluoro or iodo or lower alkyl such as methyl, ethyl or propyl;
- $R_3$ is hydrogen or, when $R_2$ is other than hydrogen, halo or lower alkyl; and
- $R_4$ and $R_5$ are hydrogen or lower alkyl.

Also included are acid addition salts of the basic compounds of Formula I with pharmaceutically acceptable acids said salts having the same pharmacodynamic activity of the bases with non-limiting side effects. Exemplary of such organic or inorganic acids are maleic, malic, fumaric, succinic, methanesulfonic, ethanedisulfonic, salicyclic, citric, hydrochloric, sulfamic, phosphoric, nitric, sulfuric or hydrobromic acids. Other solvates such as hydrates may also be present. The salts are prepared by methods known to the art such as reacting the base with an excess of acid in a lower alkyl alcohol or a similar organic solvent.

The term "lower alkyl", whenever used in the definition of the compounds of Formula I, is meant to contain from 1–4 carbon atoms. Also O-alkanoyl esters having from 2–6 carbon atoms in each alkanoyl group may be prepared by methods known to the art, such as reaction with an alkanoyl halide in the presence of a tertiary organic base, with any reactive nitrogen centers such as the 3 ring member or the amino portion of the sulfamyl group protected. Exemplary of such O-alkanoyl derivatives are acetyl, valeryl, isobutyryl or propionyl.

It will be obvious to one skilled in the art that the compounds of Formula I may be present as diastereoisomers which may be resolved into d, l optical isomers. Resolution of the optical isomers may be conveniently accomplished by fractional crystallization of their salts with optically active acids from appropriate solvents. Unless otherwise specified herein or in the claims, it is intended to include all isomers, whether separated or mixtures thereof. Where isomers are separated, the desired pharmacological activity will usually predominate in one of the isomers.

A subgeneric group of this invention comprises the compounds of Formula I in which $R_1$ and $R_2$ are as defined above; $R_3$ is hydrogen, and $R_4$ and $R_5$ are hydrogen. These compounds have pronounced peripheral dopaminergic activity and increase renal blood flow.

The new compounds of Formula I have pharmaceutical activity such as hypotensive, antibacterial, antidepressant and analgetic activity as is common with similar compounds of the art, Swiss Pat. No. 555,831. They also may be used as chemical intermediates such as for preparing 3-substituted compounds which in turn have hypotensive or analgetic activity, U.S. Pat. No. 3,496,166. The compounds of Formula I in which $R_3$ is hydrogen also have dopaminergic activity as is disclosed more specifically below.

The compounds of this invention are prepared by the following last step reactions:

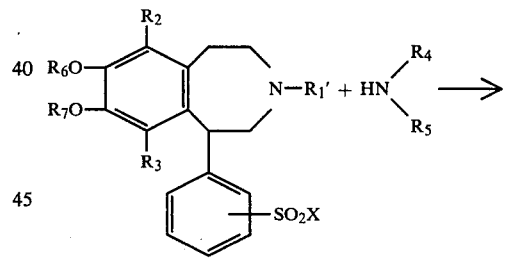

II

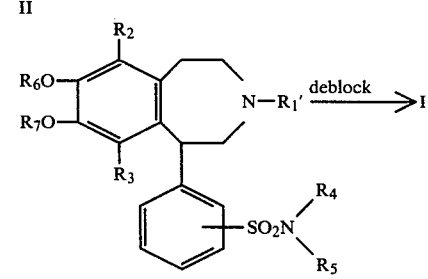

III

The intermediates of Formula II have $R_2$, $R_3$, $R_4$ and $R_5$ as defined for Formula I; X is chloro or bromo; $R_1'$ is lower alkyl, allyl or a N-protecting group such as trichloroacetyl, benzyloxycarbonyl, trifluoroacetyl or benzyl; $R_6$ and $R_7$ are lower alkyl of 1–4 carbons especially methyl or, when taken together, ethylene or especially methylene.

The term "N-protecting group" is used to indicate that the 3-substituent is inserted to prevent the chemically reactive hydrogen on the ring nitrogen member of the intermediate (II) from being affected during reaction. It is then removed after the desired chemical reaction by standard reactions to regenerate the secondary amine. Such groups are commonly used in the polypeptide or antibiotic arts. Groups commonly used are tert.-butoxycarbonyl, trichloroethoxycarbonyl, p-methoxybenzylcarbonyl, isobornyloxycarbonyl, trityl, benzhydryl and others suitable for protecting a secondary amino function. Reference to the use of other protecting groups for N or O functions may be had to "Protective Groups in Organic Chemistry", J. F. W. McOmie, Plenum Press, New York 1973.

The reaction, II→III, is run in an organic solvent inert to the reactants and in which the reactants are soluble such as dimethylformamide, dimethylacetamide, tetrahydrofuran or dimethylsulfoxide. The amine reactant,

is usually employed in excess. The reaction is carried out at any convenient temperature until completion. For example a temperature chosen from the range of about 0° C. to room temperature is most convenient. Compound III may be isolated by methods known to the art or may be reacted further without purification to remove any blocking group represented by $R_1'$, $R_6$ or $R_7$ by methods known to the art.

The following reaction sequence illustrates the overall series of reactions which is conveniently used to prepare the compounds of this invention:

SEQUENCE A

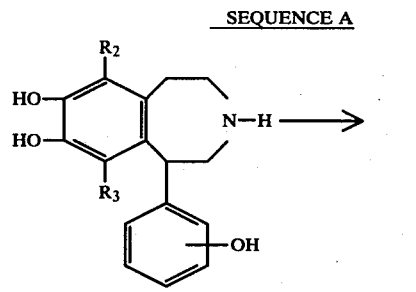

(1)

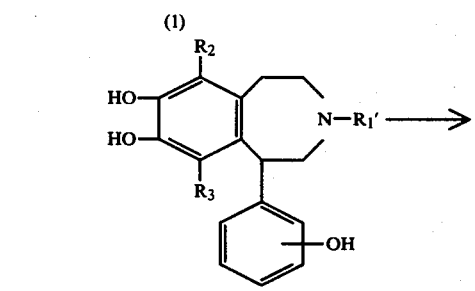

(2)

-continued

SEQUENCE A

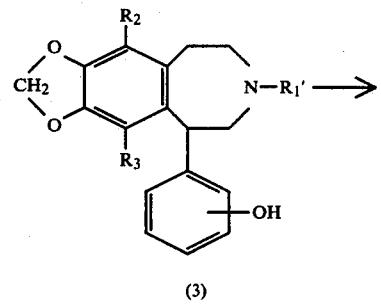

(3)

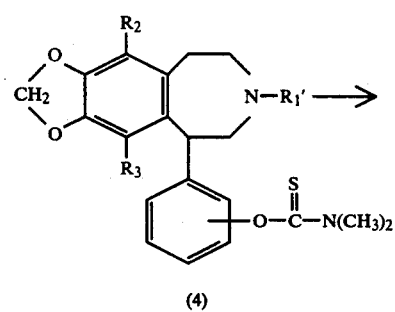

(4)

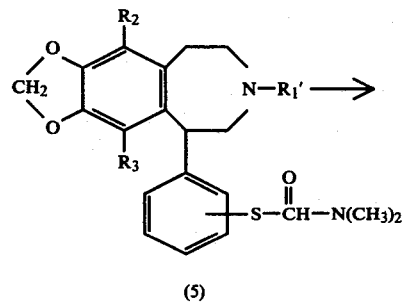

(5)

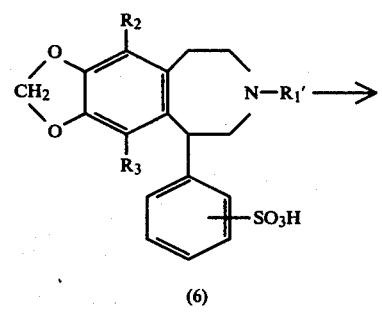

(6)

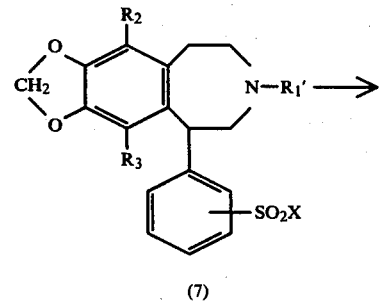

(7)

-continued
SEQUENCE A

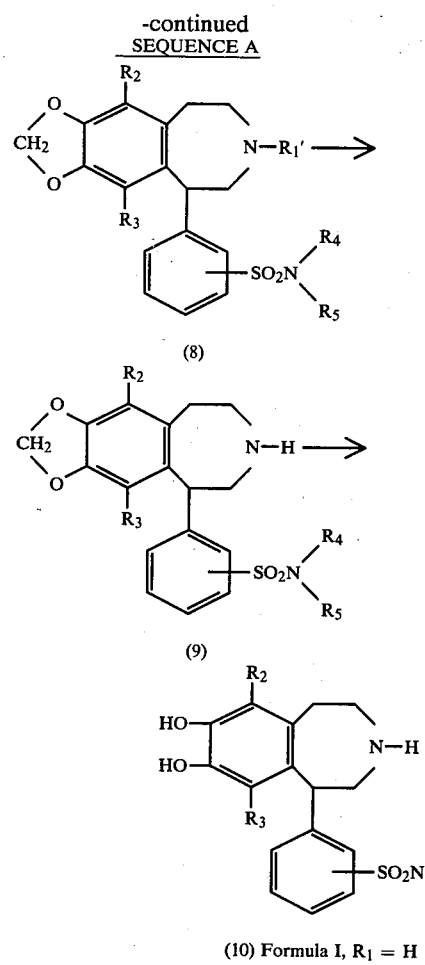

(10) Formula I, $R_1$ = H

In reaction sequence A, $R_1'$ is a protective group for a secondary nitrogen as described above. In the illustrative sequence, if the starting material (1) has a structure with a 3-allyl or lower alkyl substituent, there is no need for using such a protective group. $R_2$, $R_3$, $R_4$, $R_5$ and X are as defined above.

The preparation is dependent on a sulfur-oxygen interchange reaction (4→5) to introduce the sulfur function directly onto the 1-phenyl ring. The appropriate starting materials (1) are known to the art (U.S. Pat. No. 4,171,359, German patent application No. 2849766 or Belgium Pat. No. 860,774).

The protective means for the 7,8-dihydroxy groups is conveniently the methylene (—CH₂—) link as illustrated above. This system is easily produced in good yield by the selective reaction of a methylene dihalide at the 7,8-position of the appropriate triol (2). The ethylenedioxy system is also conveniently used for this reason by reaction with an ethylene dihalide. 7,8-Di-lower-alkoxy-1-(hydroxyphenyl)-2,3,4,5-tetrahydro-1H-3-benzazepines are less convenient to prepare because of a lack of selectivity in the formation of the ether derivative. They are, however, available in the prior art and can be alternatively used.

The second illustrative sequence for preparing the compounds of this invention comprises the formation of the 7,8-dialkoxy-1-phenyl-2,3,4,5-tetrahydro-1H-3-benzazepine nucleus with a sulfur function present on the phenyl ring which function may then be converted optionally to the various sulfamyl groups which characterize the structures of the compounds of this invention.

SEQUENCE B

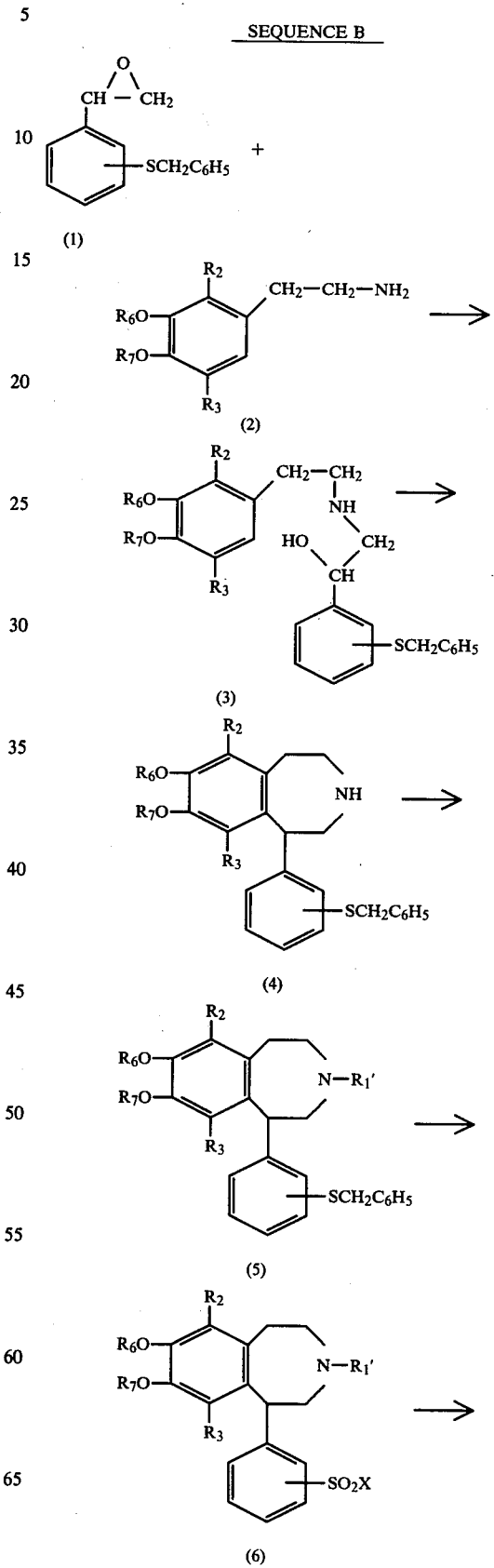

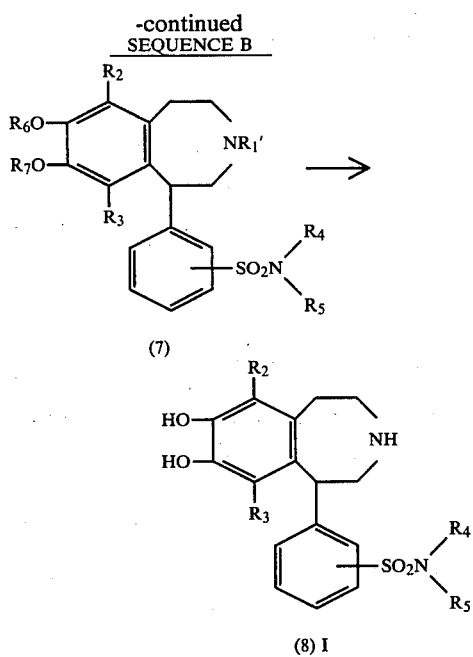

Reaction sequence B is particularly adaptable to the use of the 7,8-dialkoxy-system of protecting the 7,8-dihydroxy groups however the methylenedioxy or ethylenedioxy derivatives are equally useful for this purpose. The symbols are as defined above.

Another aspect of this invention are the new chemical compounds which are useful as intermediates for preparing compounds of formula I. Their 3-benzazepine structures are characterized in the 1-phenyl ring by a sulfonic acid group, a sulfonic acid halide group or certain thio-containing groups useful for generating such sulfonic acid groups by chemical reaction illustrated here. These are of the structural formula:

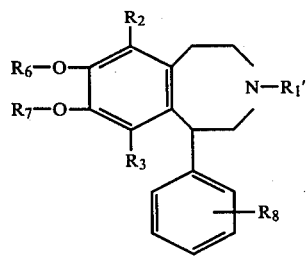

in which $R_1'$, $R_2$, $R_3$, $R_6$ and $R_7$ are as defined and $R_8$ is —$SO_3H$, —$SO_2Cl$, —$SO_2Br$, —S—$CH_2C_6H_5$ or

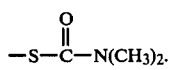

Of particular interest are the compounds in which $R_3$ is hydrogen, $R_2$ is halo, $R_6$ and $R_7$, when taken together, are methylene or ethylene and $R_8$ is —$SO_3H$, —$SO_2Cl$ or

The new compounds of this invention of Formula I in which $R_3$ is hydrogen are of particular interest in having activity as antihypertensive agents due to a renal dopaminergic mechanism. In a single preliminary screening test the exemplified compound in which $R_2$ and $R_3$ are chloro demonstrated no renal dopaminergic activity.

The active dopaminergic compounds which are part of this invention therefore stimulate peripheral dopamine receptors, for example, they increase renal blood flow and have as an end result antihypertensive activity. This renal vasodilator activity of the designated benzazepine compounds of Formula I is measured in an anesthetized dog. In this pharmacological procedure, a test compound is administered at progressively increasing (3-fold) infusion rates beginning at 0.1 mcg/kg/min up to 810 mcg/kg/min for 5 minutes each to anesthetized normotensive dogs and the following parameters are measured: renal artery blood flow, iliac artery blood flow, arterial blood pressure and heart rate. Results are reported as a percent change, increase or decrease, at time of peak response (from pre-drug controls), and for a significant effect renal blood flow (increase) and renal vascular resistance (decrease) should be approximately 10% or greater. The effect on renal vascular resistance can be calculated from any change in renal blood flow and arterial blood pressure. To confirm the mechanism of action, representative active renal vasodilator compounds are checked for blockade by bulbocapnine which is known to be a specific blocker of renal dopamine receptors. Dopamine is run as a positive control in each screening procedure.

A representative compound of this invention, 6-chloro-7,8-dihydroxy-1-(p-sulfamylphenyl)-2,3,4,5-tetrahydro-1H-3-benzazepine hydrobromide, demonstrated the following data:

| DRUG | DOSE (μg/Kg/min) | MAP* (arterial blood pressure) | RBF* (renal blood flow) | RVR* (renal vascular resistance) | HR* (heart rate) |
|---|---|---|---|---|---|
| Dopamine | 3 | −4.9 | +38.1 | −31.6 | +0 |
| Test compound | 3 | −3.6 | +17.0 | −18.0 | −2.9 |
|  | 30 | −6.6 | +41.0 | −33.7 | −6.3 |
|  | 300 | −10.6 | +16.0 | −22.7 | +3.3 |

*% change from control value recorded before each infusion in one dog.

In four dogs the $ED_{15}$ was 20 μg/kg (dopamine, 3.5 μg/kg). In a phosphate-mannitol dog test the compound demonstrated blood pressure lowering at 5 mg/p.o.

6-Chloro-7,8-dihydroxy-1-(4-N,N-dimethylsulfamylphenyl)-2,3,4,5-tetrahydro-1H-3-benzazepine hydrobromide hydrate:

| Test compound | 3 | 0 | +6.7 | −6.2 | 0 |
|---|---|---|---|---|---|
|  | 30 | −1.4 | +6.3 | −6.8 | +6.7 |
|  | 300 | −15.7 | −6.3 | −9.6 | +10.0 |

6,9-Dichloro-7,8-dihydroxy-1-(p-sulfamylphenyl)2,3,4,5-tetrahydro-1H-3-benzazepine hydrobromide hydrate.

| Test compound | 3 | 0 | 0 | 0 | +5.9 |
|---|---|---|---|---|---|
|  | 30 | +1.3 | 0 | +1.4 | +6.3 |
|  | 300 | +0.6 | +6.3 | −5.1 | +6.3 |

The benzazepine compounds of Formula I which are able to cross the blood-brain barrier also have antiparkinsonism activity due to central dopaminergic activity as demonstrated by employing a modified standard animal pharmacological test procedure reported by Ungerstedt et al., in *Brain Research* 24, 1970, 485-493. This procedure is based on a drug induced rotation of rats having extensive unilateral lesions of the substantia nigra. Briefly, the test comprises the quantitative recording of rotational behavior in rats in which 6-hydroxydopamine lesions of the nigrostriatal dopamine system have been produced. A unilateral brain lesion in the left substantia nigra causes the dopamine receptor in the left caudate to become hypersensitive following the resulting degeneration of the nigral cell bodies. These lesions destroy the source of the neurotransmitter dopamine in the caudate but leave the caudate cell bodies and their dopamine receptors intact. Activation of these receptors by drugs which produce contralateral rotation, with respect to the lesioned side of the brain, is used as a measure of central dopaminergic activity of the drug.

Compounds which are known to be clinically effective in controlling parkinsonism, such as, for example, L-dopa and apomorphine, are also effective in this rate turning model. These compounds directly activate the dopamine receptors and cause contralateral rotation of the lesioned rat.

The pharmaceutical compositions using the new compounds of this invention having pharmaceutical activity are prepared in conventional dosage unit forms by incorporating a compound of Formula I, an isomer or a pharmaceutically acceptable acid addition salt or ester thereof, with a nontoxic pharmaceutical carrier according to accepted procedures in a nontoxic amount sufficient to produce the desired pharmaceutical activity in a subject, animal or human. Preferably the compositions will contain the active ingredient in an active but nontoxic amount selected from about 15 mg to about 1000 mg, preferably 25–250 mg, of active ingredient per dosage unit but this quantity depends on the specific biological activity desired and the conditions of the patient.

The pharmaceutical carrier employed may be, for example, either a solid or liquid. Exemplary of solid carriers are lactose, terra alba, sucrose, talc, gelatin, agar, pectin, acacia, magnesium stearate, stearic acid, and the like. Exemplary of liquid carriers are syrup, peanut oil, olive oil, water and the like. Similarly the carrier or diluent may include any time delay material well known to the art, such as glyceryl monostearate or glyceryl distearate alone or with a wax.

A wide variety of pharmaceutical forms can be employed. Thus, if a solid carrier for oral administration is used the preparation can be tableted, placed in a hard gelatin capsule in powder or pellet form, or in the form of a troche or lozenge. The amount of solid carrier will vary widely but preferably will be from about 25 mg to about 1 g. If a liquid carrier is used, the preparation will be in the form of a syrup, emulsion, soft gelatin capsule, sterile injectable liquid such as an ampul, or an aqueous or nonaqueous liquid suspension.

The pharmaceutical preparations are made following the conventional techniques of the pharmaceutical chemist involving mixing, granulating and compressing when necessary, or variously mixing and dissolving the ingredients as appropriate to give the desired end product.

The method of producing the pharmaceutical activity in accordance with this invention comprises administering internally to a subject in need of such activity a compound of Formula I or a pharmaceutically acceptable acid addition salt thereof, usually combined with a pharmaceutical carrier, in a nontoxic amount sufficient to produce said activity as described above. The route of administration may be any route which effectively transports the active compound to the site of action such as orally, rectally or parenterally, the oral route being preferred. Advantageously, equal doses will be administered several times such as two or three times a day with the daily dosage regimen being selected from about 50 mg to about 2 g. When the method described above is carried out antihypertensive or other designated activities are produced with a minimum of side effects.

The following examples are designed solely to illustrate the preparation and use of the compounds of this invention. The temperatures are Centigrade. Other variations of these examples will be obvious to those skilled in the art.

EXAMPLE 1

Forty-two grams (0.104 mole) of 6-chloro-7,8-dihydroxy-1-(p-hydroxyphenyl)-2,3,4,5-tetrahydro-1H-3-benzazepine methane sulfonate (Belgium Pat. No. 860, 774) was suspended in 1 l. of dry toluene and 30.0 ml of dry acetonitrile then 100 ml (0.77 mole) of trifluoroacetic anhydride was added rapidly. The mixture was stirred overnight to give a clear solution which was concentrated in vacuo to an oil. This was dissolved in methylene chloride. The solution was then washed twice with water, several times with 5% sodium bicarbonate solution and then with brine. The dried extract was concentrated to give an oil, 6-chloro-7,8-dihydroxy-1-(p-hydroxyphenyl)-2,3,4,5-tetrahydro-1H-3-benzazepine trifluoroacetamide (44 g) which was judged to be sufficiently pure by NMR and TLC for further use.

A solution of 44 g (0.104 mole) of 6-chloro-7,8-dihydroxy-1-(p-hydroxyphenyl)-2,3,4,5-tetrahydro-1H-3-benzazepine trifluoroacetamide in 700 ml of dry dimethylformamide was treated with 45.5 g (0.784 mole) of potassium fluoride. After five minutes, 11.2 ml (27.6 g, 0.109 mole) of dibromomethane was added. The mixture was heated at 115° and held at 115° for 6 hours. The reaction mixture was concentrated. The residue was dissolved in ethyl acetate and washed several times with water. The dried, concentrated product was chromatographed over 800 g of silica gel with a 1 to 3% methanol in chloroform gradient. The homogeneous fractions gave 30.4 g (71%) of 6-chloro-7,8-methylenedioxy-1-(p-hydroxyphenyl)-2,3,4,5-tetrahydro-1H-3-benzazepine trifluoroacetamide. A sample was crystallized from acetonitrile to give white crystals, m.p. 191°–193°.

Substituting ethylenedibromide for dibromomethane gives the 7,8-ethylenedioxy congener which then is used in the subsequent steps in equimolar quantities. Other reactive dihalomethanes or ethanes are also used similarly.

A solution of 12.6 g (0.031 mole) of 6-chloro-7,8-methylenedioxy-1-(p-hydroxyphenyl)-2,3,4,5-tetrahydro-1H-3-benzazepine trifluoroacetamide in 100 ml of dry dimethylformamide was treated first with 15.2 g (0.136 mole) of triethylene diamine and then with 6.27 g (0.051 mole) of dimethylthiocarbamoyl chloride. The mixture was stirred at room temperature for four hours, poured onto 500 ml of ice water and the precipitate was filtered and washed well with water. The solid was dissolved in 95% ethanol, treated with charcoal, filtered and diluted with water to the cloud point. Chilling gave a total of 11.3 g (73%) of 6-chloro-7,8-methylenedioxy-1-(p-O-dimethylthiocarbamoylphenyl)-2,3,4,5-tetrahydro-1H-3-benzazepine trifluoroacetamide, m.p. 128°–131°.

Diphenyl-diphenyloxide eutectic (Dowtherm "A", 200 ml) was preheated to 200° in an oil bath then 24.0 g (0.048 mole) of 6-chloro-7,8-methylenedioxy-1-(p-O-dimethylthiocarbamoylphenyl)-2,3,4,5-tetrahydro-1H-3-benzazepine trifluoroacetamide was added in portions to the rapidly stirring mixture. The resulting solution was heated for about ten hours at 205°–230°. The cooled reaction was poured directly on a column packed with 800 g of silica gel which had been washed with cyclohexane. The column was developed with cyclohexane to remove the heat transfer medium then with a gradient of 3/1, then 5/2 of cyclohexane-ethyl acetate to give the homogeneous product. Crystallization from acetonitrile gave 8.7 g (40%) of 6-chloro-7,8-methylenedioxy-1-(p-S-dimethylcarbamoylphenyl)-2,3,4,5-tetrahydro-1H-3-benzazepine trifluoroacetamide, m.p. 194°–195°.

Ten grams (0.02 mole) of 6-chloro-7,8-methylenedioxy-1-(p-S-dimethylcarbamoylphenyl)-2,3,4,5-tetrahydro-1H-3-benzazepine trifluoroacetamide was suspended in 200 ml of 90% formic acid and 35 ml of 30% hydrogen peroxide was added dropwise with stirring at room temperature. The mixture was stirred for 18 hours. The clear solution was evaporated and the residue therefrom was azeotroped several times with 95% ethanol. The crude product was dissolved in ethyl acetate, washed with cold 1% hydrochloric acid and brine, then concentrated to about 10 g of crude 6-chloro-7,8-methylenedioxy-1-(p-sulfophenyl)-2,3,4,5-tetrahydro-1H-3-benzazepine trifluoroacetamide, NMR was consistent with structure and high pressure liquid chromatography on a C-18 reverse phase column with a 60/40/1 water-methanol-acetic acid containing $3 \times 10^{-5}$ M of sodium hexanesulfonate showed the product to be at least 85% pure.

A mixture of 1.0 g (2.1 mmole) of the crude 6-chloro-7,8-methylenedioxy-1-(p-sulfophenyl)-2,3,4,5-tetrahydro-1H-3-benzazepine trifluoroacetamide, 20 ml of thionyl chloride and 0.04 ml of dimethylformamide was heated at 80° for 2 hours. The thionyl chloride was evaporated in vacuo. The residue which is 6-chloro-7,8-methylenedioxy-1-(p-chlorosulfonylphenyl)-2,3,4,5-tetrahydro-1H-3-benzazepine trifluoroacetamide was dissolved in tetrahydrofuran. The solution was added slowly to 40 ml of iced concentrated ammonium hydroxide. The mixture was stirred at room temperature for an hour, the pH was adjusted to 8 with hydrochloric acid and the product was extracted into ethyl acetate. The extracts were washed with water, dried, concentrated and applied to a column packed with 50 g of silica gel. The column was developed with a gradient of 24 to 35 percent of ethyl acetate in cyclohexane to give 0.5 g of 6-chloro-7,8-methylenedioxy-1-(p-sulfamylphenyl)-2,3,4,5-tetrahydro-1H-3-benzazepine trifluoroacetamide. Field desorption mass spectroscopy showed an intense m/e at 476 which is consistent with the molecular ion. NMR and IR were consistent with the structure.

Substituting ethylamine for ammonia gives the (p-N-ethylsulfamylphenyl) derivative. This following alkali hydrolysis and boron tribromide treatment as detailed hereafter gives 6-chloro-7,8-dihydroxy-1-(p-N-ethylcarbamylphenyl)-2,3,4,5-tetrahydro-1H-3-benzazepine hydrobromide.

A mixture of 0.5 g (1.1 mmole) of 6-chloro-7,8-methylenedioxy-1-(p-sulfamylphenyl)-2,3,4,5-tetrahydro-1H-3-benzazepine trifluoroacetamide, 0.1 g of sodium hydroxide and 50 ml of methanol was stirred at room temperature for 2 hours, poured into water and extracted with ethyl acetate. The combined extracts were washed with brine, dried and concentrated. The residue was chromatographed on 20 g of silica gel with a gradient of 1% to 5% of methanol in chloroform to give 0.35 g of pure 6-chloro-7,8-methylenedioxy-1-(p-sulfamylphenyl)-2,3,4,5-tetrahydro-1H-3-benzazepine. This was suspended in 5 ml of dry methylene chloride, cooled to −60° C. and a solution of 5 ml of boron tribromide in methylene chloride (1 g/ml) was added dropwise with stirring under a nitrogen atmosphere. The mixture was stirred for about an hour at room temperature, recooled to −15° when excess methanol was added cautiously. The solvents were evaporated. The residue was azeotroped several times with methanol. The remaining solid was crystallized from methanol-acetonitrile ether to give 0.36 g (86%) of 6-chloro-7,8-dihydroxy-1-(p-sulfamylphenyl)-2,3,4,5-tetrahydro-1H-3-benzazepine hydrobromide, m.p. 289°–290°.

The base (1 g) is regenerated using dilute sodium bicarbonate-isopropanol. Aliquots of 100 mg of the base in isopropanol are treated with methane sulfonic or hydrochloric acid to give the methane sulfonic acid or hydrochloride salts.

EXAMPLE 2

A mixture of 5.0 g (0.011 mole) of 6-chloro-7,8-methylenedioxy-1-(p-sulfophenyl)-2,3,4,5-tetrahydro-1H-3-benzazepine trifluoroacetamide, 70 ml of thionyl chloride and 0.08 ml of dimethylformamide was heated at 80° for 2 hours, the solvents were evaporated in vacuo.

The acid chloride residue was dissolved in tetrahydrofuran. This solution was added slowly to a solution of dimethylamine in tetrahydrofuran at −15°. The reaction was stirred at 0° for an hour then allowed to reach room temperature over 20 minutes. Hydrochloric acid was added to pH 6.5. The product was extracted into chloroform. The extracts were washed well with water, dried and concentrated to 4.0 g of crude product. This was chromatographed on 120 g of silica gel with a gradient of 25% to 33% of ethyl acetate in cyclohexane. The homogeneous fractions were crystallized from aqueous ethanol to give 3.1 g (78%) of 6-chloro-7,8-methylenedioxy-1-(p-N,N-dimethylsulfamyl-phenyl)-2,3,4,5-tetrahydro-1H-3-benzazepine trifluoroacetamide, m.p. 143°–145°.

A solution of 2.3 g (0.00457 mole) of 6-chloro-7,8-methylenedioxy-1-(p-N,N-dimethylsulfamylphenyl)-2,3,4,5-tetrahydro-1H-3-benzazepine trifluoroacetamide, 75 ml of methanol and 0.5 g of sodium hydroxide was stirred at room temperature for 2 hours, diluted with water and extracted several times with ethyl acetate. The extracts were washed with brine, dried and concentrated. The crude residue was chromatographed on 75 g of silica gel with a gradient of 1% to 4% of methanol in chloroform. The homogeneous cuts were combined and concentrated to give 1.4 g (75%) of 6-chloro-7,8-methylenedioxy-1-(p-N,N,-dimethylsulfamylphenyl)-2,3,4,5-tetrahydro-1H-3-benzazepine. A field description mass spectrogram showed an intense peak for m/e of 408 which is consistent with the structure. NMR and IR spectra also agreed with the structure.

This product (300 mg) was dissolved in 15 ml of dry methylene chloride, the solution was cooled to −15° under a nitrogen atmosphere. A solution of 3 ml of boron tribromide in methylene chloride (1 g/5 ml) was added dropwise. A precipitate formed very quickly. The mixture was then stirred at room temperature for about an hour and recooled in an ice bath. Excess methanol was added carefully. The resulting solution was evaporated. The residue was azeotroped several times with methanol. The solid was crystallized from methanol/acetonitrile to give off white crystals of 6-chloro-7,8-dihydroxy-1-(p-N,N,-dimethylsulfamyl-phenyl)-2,3,4,5-tetrahydro-1H-3-benzazepine hydrobromide, m.p. 238°–240°. The NMR and IR spectra are compatible with structure.

EXAMPLE 3

A solution of 50 g (0.219 mole) of p-thiobenzylbenzoic acid in 450 ml of dry tetrahydrofuran was cooled in ice water under a nitrogen atmosphere and a solution of 400 ml of 1 M diborane in tetrahydrofuran (0.4 mole) was added dropwise. After a half hour, the cooling bath was removed. The mixture was stirred at room temperature for 2 hours. The reaction was recooled in ice water and excess methanol was added cautiously. The solvents were evaporated to give a white solid which was crystallized from aqueous ethanol to give 39.5 g (79%) of p-thiobenzylbenzyl alcohol, m.p. 87°–88.5°.

A solution of 38.5 g (0.167 mole) of p-thiobenzylbenzyl alcohol in 400 ml of toluene was treated with 100 g of activated manganese dioxide. The suspension was stirred and heated in an oil bath for 5 hours with a Dean-Stark water separator. The mixture was cooled slightly, filtered through a filter aid with chloroform. The filtrate was concentrated to a pale yellow solid. This was crystallized from absolute alcohol to give 30.1 g (80%) of p-thiobenzylbenzaldehyde, m.p. 62°–63.5°.

A solution of 30.0 g (0.132 mole) of p-thiobenzylbenzaldehyde, 37.6 g (0.184 mole) of trimethylsulfonium iodide and 150 ml of dry dimethylsulfoxide (held under a nitrogen atmosphere) was added over 15 minutes a solution of 18.6 g (0.17 mole) of potassium t-butoxide in 100 ml of dry dimethylsulfoxide. The mixture was stirred an additional 45 minutes at room temperature and poured into 3 l. of iced water. The quench was extracted with ethyl acetate (4×300 ml). The combined organic extracts were washed with brine and water (4 times) dried over magnesium sulfate. The extracts were concentrated to solid p-thiobenzylstyrene oxide.

This crude epoxide was mixed with 28.5 g (0.13 mole) of 2-chlorohomoveratrylamine and heated at 110° (under nitrogen) for 18 hours. The crude product was dissolved in a little chloroform and applied to a column packed with 900 g of silica gel. The column was developed with a gradient of chloroform to 2½% of methanol in chloroform taking 400 ml fractions. The homogeneous product was crystallized from absolute alcohol to give 15.4 g of α-[N-2-chloro-3,4-dimethoxyphenethyl-amino methyl]-4′-thiobenzylbenzyl alcohol, m.p. 80°–81.5°.

A solution of 13.0 g (0.0284 mole) of the benzyl alcohol in 260 ml of dry methylene chloride was treated with 10.4 ml of methanesulfonic acid. The resulting solution was gently refluxed for 3 hours. Ice was added followed by 150 ml of 10% sodium hydroxide solution. The organic layer was separated. The aqueous layer was extracted with methylene chloride and the combined organic extracts were washed with water, dried and concentrated to leave 12.1 g of crude product which was chromatographed on 650 g of silica gel with a gradient of 2% to 4% of methanol in chloroform. This gave 9.4 g (75%) of 6-chloro-7,8-dimethoxy-1-(p-thiobenzylphenyl)-2,3,4,5-tetrahydro-1H-3-benzazepine. NMR, IR and mass spectra agreed with the structure.

The benzazepine, 7.7 g (0.017 mole), was dissolved in 80 ml of acetone and 20 ml of water then a solution of 5.3 g of sodium carbonate in 10 ml of water was added. The mixture was cooled in ice water. A solution of 5.44 g of benzyl chloroformate in 25 ml of acetone was added dropwise. The mixture was stirred at 5° for one hour, then overnight at room temperature. Water was added. The product was extracted into ethyl acetate and washed with brine and water. The concentrated product was chromatographed on 200 g of silica gel with a gradient of chloroform to 0.5% of methanol in chloroform to give 4.5 g (46%) of 6-chloro-7,8-dimethoxy-1-(p-thiobenzylphenyl)-2,3,4,5-tetrahydro-1H-3-benzazepine benzylcarbamate as a syrup. The field desorption mass spectroscopy indicated an intense m/e of 573 which is compatible with the structure. The IR and NMR spectra were consistent.

The carbamate (4.5 g, 0.0079 mole) was dissolved in 45 ml of glacial acetic acid and 0.45 ml of water was added. The solution was cooled in water (15°). Chlorine gas was bubbled through the solution for 20 minutes while maintaining the reaction temperature between 25° and 27°. Then the mixture was stirred at room temperature for 15 minutes, poured onto 150 ml of ice water and extracted quickly with chloroform. The combined extracts were washed with water and nitrogen was bubbled through the slightly wet solution. The solvent was evaporated at room temperature in vacuo to give a residue of 6,9-dichloro-7,8-dimethoxy-1-(p-chlorosulfonylphenyl)-2,3,4,5-tetrahydro-1H-3-benzazepine benzylcarbamate.

The acid chloride residue was dissolved in tetrahydrofuran then added to 75 ml of iced ammonium hydroxide. After being stirred for 2 hours at room temperature, the pH was adjusted to about 8 with hydrochloric acid. The product was extracted into chloroform and washed with water. The dried concentrate was chromatographed on 200 g of silica gel with a gradient of chloroform to 1% of methanol in chloroform to give 3.24 g (75%) of 6,9-dichloro-7,8-dimethoxy-1-(p-sulfamylphenyl)-2,3,4,5-tetrahydro-1H-3-benzazepine benzylcarbamate as an oil. The NMR, IR and mass spectra agreed with the structure.

The sulfamyl derivative (2.0 g, 3.56 mmole) was dissolved in 60 ml of dry methylene chloride. The solution was cooled to −15% (under nitrogen). A solution of 17.7 ml of boron tribromide in methylene chloride (1 g/5 ml) was added dropwise. The solution was then stirred at room temperature to produce a precipitate. After about an hour the mixture was recooled, methanol was added slowly and the solution was concentrated and azeotroped with additional methanol. The residual product was dissolved in a little acetone and added dropwise to a stirred solution of 3 parts of ether and one part of ethyl acetate to afford an off white powder, 0.586 g (35%), m.p. 210°–212° of 6,9-dichloro-7,8-dihydroxy-1-(p-sulfamylphenyl)-2,3,4,5-tetrahydro-1H-3-benzazepine hydrobromide.

The crude acid chloride product (200 mg) (obtained by evaporating the chloroform extract prior to treatment with ammonia in the above procedure) is treated with dilute sodium carbonate solution/dimethylformamide. Evaporation and extraction with methylene chloride is followed by washing and drying the extract. Evaporation gives 6,9-dichloro-7,8-dimethoxy-1-(p-sulfophenyl)-2,3,4,5-tetrahydro-1H-3-benzazepine benzylcarbamate. Alkaline hydrolysis and boron tribromide treatment gives 6,9-dichloro-7,8-dihydroxy-1-(p-sulfophenyl)-2,3,4,5-tetrahydro-1H-3-benzazepine. Alternatively the O,O,N-protected sulfonic acid is treated with phosphorus pentabromide to give the 1-(p-bromosulfonylphenyl) compound which is reacted with ammonium hydroxide. Hydrolysis and de-etherification gives 6,9-dichloro-7,8-dihydroxy-1-(p-sulfamylphenyl)-2,3,4,5-tetrahydro-1H-3-benzazepine hydrobromide.

EXAMPLE 4

6-Methyl-7,8-dihydroxy-1-(p-hydroxyphenyl)-2,3,4,5-tetrahydro-1H-3-benzazepine hydrobromide (21 g, German patent application No. 2849766) in toluene-acetonitrile is reacted with 50 ml of trifluoroacetic anhydride. The N-protected product is isolated by concentration in vacuo. This crude material (11 g) is reacted with 12 g of potassium fluoride in dimethylformamide then with 7.2 g of dibromomethane at 100° for 6 hours. The mixture is evaporated and the residue purified as described in Example 1 to give 6-methyl-7,8-methylenedioxy-1-(p-hydroxyphenyl)-2,3,4,5-tetrahydro-1H-3-benzazepine trifluoroacetamide.

This material (4 g) is O-acylated using base and dimethylthiocarbamoyl chloride to give the 1-(p-O-dimethylthiocarbamoylphenyl) compound which (~1.5 g) is heated in diphenyl-diphenyloxide eutectic at 215° to give the S-dimethylcarbamoyl intermediate. Oxidation of this material (1.2 g) using 5 ml of hydrogen peroxide at room temperature in concentrated formic acid solution for 24 hours gives 6-methyl-7,8-methylenedioxy-1-(p-sulfophenyl)2,3,4,5-tetrahydro-1H-3-benzazepine trifluoroacetamide.

The sulfonic acid (750 mg) is converted to the sulfonyl chloride using thionyl chloride/dimethylformamide then reacted without purification with an excess of ammonium hydroxide to give 6-methyl-7,8-methylenedioxy-1-(p-sulfamylphenyl)-2,3,4,5-tetrahydro-1H-3-benzazepine trifluoroacetamide. Alkaline hydrolysis of the acetamide (500 mg) and boron tribromide treatment of the residue in the cold gives the desired 6-methyl-7,8-dihydroxy-1-(p-sulfamylphenyl)-2,3,4,5-tetrahydro-1H-3-benzazepine hydrochloride.

EXAMPLE 5

Using the reactions of Examples 1 and 4 but starting with 6-propyl-7,8-dihydroxy-1-(p-hydroxyphenyl)-2,3,4,5-tetrahydro-1H-3-benzazepine methanesulfonate (German patent application 2849766) gives 6-propyl-7,8-methylenedioxy-1-(p-sulfophenyl-2,3,4,5-tetrahydro-1H-3-benzazepine trifluoroacetamide, its acid chloride and finally 6-propyl-7,8-dihydroxy-1-(p-sulfamylphenyl)-2,3,4,5-tetrahydro-1H-3-benzazepine hydrobromide. Using as starting material 6-chloro-7,8-dihydroxy-1-(2-hydroxyphenyl)-2,3,4,5-tetrahydro-1H-3-benzazepine hydrochloride (Belgium Pat. No. 860,774) gives 6-chloro-7,8-ethylenedioxy-1-(o-sulfophenyl)-2,3,4,5-tetrahydro-1H-3-benzazepine trifluoroacetamide, its acid chloride and finally 6-chloro-7,8-dihydroxy-1-(o-sulfamylphenyl)-2,3,4,5-tetrahydro-1H-3-benzazepine hydrobromide. Using as starting material 6-chloro-7,8-dihydroxy-1-(3-hydroxyphenyl)-2,3,4,5-tetrahydro-1H-3-benzazepine hydrobromide (Belgium Pat. No. 860,774) gives 6-chloro-7,8-methylenedioxy-1-(m-sulfophenyl)-2,3,4,5-tetrahydro-1H-3-benzazepine trifluoroacetamide, its acid chloride and finally 6-chloro-7,8-dihydroxy-1-(m-N-butylsulfamylphenyl-2,3,4,5-tetrahydro-1H-3-benzazepine hydrobromide. Using 6-bromo-7,8-dihydroxy-1-(p-hydroxyphenyl)-2,3,4,5-tetrahydro-1H-3-benzazepine hydrobromide (Belgian Pat. No. 860,774) gives 6-bromo-7,8-methylenedioxy-1-(p-sulfophenyl)-2,3,4,5-tetrahydro-1H-3-benzazepine trifluoroacetamide, its acid chloride and finally 6-bromo-7,8-dihydroxy-1-(p-sulfamylphenyl)-2,3,4,5-tetrahydro-1H-3-benzazepine hydrobromide.

Using 7,8-dihydroxy-1-(p-hydroxyphenyl)-2,3,4,5-tetrahydro-1H-3-benzazepine hydrochloride gives 7,8-methylenedioxy-1-(p-sulfophenyl)-2,3,4,5-tetrahydro-1H-3-benzazepine trifluoroacetamide, its acid chloride and finally 7,8-dihydroxy-1-(p-sulfamylphenyl)-2,3,4,5-tetrahydro-1H-3-benzazepine hydrochloride.

Using 6-fluoro-7,8-dihydroxy-1-(p-hydroxyphenyl)-2,3,4,5-tetrahydro-1H-3-benzazepine hydrobromide (prepared as in Belgian Pat. No. 860,774, m.p. 277°) gives 6-fluoro-7,8-dihydroxy-1-(p-sulfamylphenyl)-2,3,4,5-tetrahydro-1H-3-benzazepine methylsulfonate.

EXAMPLE 6

6-Chloro-7,8-dimethoxy-1-(p-methoxyphenyl)-2,3,4,5-tetrahydro-1H-3-benzazepine (3.47 g, 0.01 mole, m.p. 140°–142.5°) in 50 ml of acetonitrile was mixed with 2.8 ml (0.02 mole) of triethylamine and 1.4 ml (0.011 mole) of allyl bromide. The mixture was heated at 85°–95° for 2½ hours. The reaction mixture was evaporated. The residue was suspended in water and extracted twice with ethyl acetate. The organic extracts were washed with water, brine and evaporated to give 2.6 g (67.2%) of a yellow oil, 3-allyl-6-chloro-7,8-dimethoxy-1-(p-methoxyphenyl)-2,3,4,5-tetrahydro-1H-3-benzazepine.

This material (2.6 g, 0.0067 mole) was dissolved in 55 ml of methylene chloride and cooled to −15° at which time 6.0 ml (0.064 m) of boron tribromide in 40 ml of methylene chloride was added slowly over ½ hour. The reaction mixture was stirred at room temperature for 3 hours, cooled and treated with an excess of methanol slowly and with cooling. The methanol was evaporated to give a foam. This was dissolved in a minimum amount of methanol and cooled. Some ethyl acetate was added to induce separation of 1.85 g (65%) of 3-allyl-6-chloro-7,8-dihydroxy-1-(p-hydroxyphenyl)-2,3,4,5-tetrahydro-1H-3-benzazepine hydrobromide, m.p. 195°–199° (dec.).

The trihydroxy compound (2.2 g) is reacted with 2 g of potassium fluoride and 1.4 g of dibromomethane in dimethylformamide with heating. Concentration and purification of the residue gives 3-allyl-6-chloro-7,8-methylenedioxy-1-(p-hydroxyphenyl)-2,3,4,5-tetrahydro-1H-3-benzazepine isolated as the hydrobromide salt.

This material (1.3 g) in dimethylformamide is reacted with an excess of triethylenediamine and dimethylthiocarbamoyl chloride at room temperature. After quenching the desired product is separated by extraction with ethanol to give 3-allyl-6-chloro-7,8-methylenedioxy-1-(p-O-dimethylthiocarbamoylphenyl)-2,3,4,5-tetrahydro-1H-3-benzazepine which (0.75 g) is heated in diphenyl-diphenyloxide at 200° for six hours.

Purification by silica gel column gives the desired thio compound which was selectively oxidized in formic acid-hydrogen peroxide to give 3-allyl-6-chloro-7,8-methylenedioxy-1-(p-sulfophenyl)-2,3,4,5-tetrahydro-1H-3-benzazepine as the hydrobromide. The sulfonic acid (1 g) is reacted with an excess of thionyl chloride with a catalytic amount of dimethylformamide at 75°. After evaporation, the crude residue is reacted with an excess of iced ammonium hydroxide. After neutralization, extraction and treatment over a silica gel column 3-allyl-6-chloro-7,8-methylenedioxy-1-(p-sulfamylphenyl)-2,3,4,5-tetrahydro-1H-3-benzazepine is isolated. Treatment with boron tribromide as described above gives 3-allyl-6-chloro-7,8-dihydroxy-1-(p-sulfamylphenyl)-2,3,4,5-tetrahydro-1H-3-benzazepine as the hydrochloride.

EXAMPLE 7

Using the same synthetic sequence as in Examples 1 and 6, but using 6-chloro-3-methyl-7,8-dihydroxy-1-(p-hydroxyphenyl)-2,3,4,5-tetrahydro-1H-3-benzazepine gives 6-chloro-3-methyl-7,8-dihydroxy-1-(p-sulfamylphenyl)-2,3,4,5-tetrahydro-1H-3-benzazepine hydrochloride. Also the 3-ethyl and 3-isobutyl congeners can be made similarly.

EXAMPLE 8

Using the reactions of Example 1 but starting with 6-fluoro-9-chloro-7,8-dihydroxy-1-(p-hydroxyphenyl)-2,3,4,5-tetrahydro-1H-3-benzazepine hydrochloride (U.S. Pat. No. 4,171,359) gives 9-chloro-6-fluoro-7,8-1-(p-sulfamylphenyl)-2,3,4,5-tetrahydro-1H-3-benzazepine hydrobromide.

Starting with 6,9-difluoro-7,8-dihydroxy-1-(p-hydroxyphenyl)-2,3,4,5-tetrahydro-1H-3-benzazepine hydrochloride (U.S. Pat. No. 4,171,359) gives 6,9-difluoro-7,8-dihydroxy-1-(p-sulfamylphenyl)-2,3,4,5-tetrahydro-1H-3-benzazepine hydrobromide.

Starting with 6-chloro-9-methyl-7,8-dihydroxy-1-(p-hydroxyphenyl)-2,3,4,5-tetrahydro-1H-3-benzazepine hydrochloride (U.S. Pat. No. 4,171,359) gives 6-chloro-9-methyl-7,8-dihydroxy-1-(p-sulfamylphenyl)-2,3,4,5-tetrahydro-1H-3-benzazepine hydrobromide.

| Ingredients | Mg. per Capsule |
| --- | --- |
| 6-Chloro-7,8-dihydroxy-1-(p-sulfamylphenyl)-2,3,4,5-tetrahydro-1H-3-benzazepine (as an acid addition salt) | 150 mg |
| Magnesium stearate | 3 mg |
| Lactose | 150 mg |

The ingredients are thoroughly mixed and placed in hard gelatin capsules. Such capsules are administered orally to subjects in need of anti-hypertensive treatment from 3–5 times daily.

What is claimed is:

1. A compound of the formula:

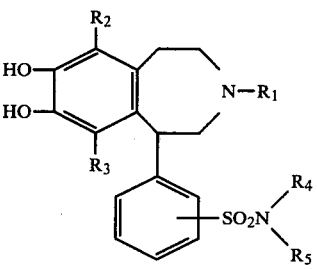

in which:

$R_1$ is hydrogen, lower alkyl of 1–4 carbons or allyl;
$R_2$ is hydrogen, halo or lower alkyl of 1–4 carbons;
$R_3$ is hydrogen, or when $R_2$ is other than hydrogen, halo or lower alkyl of 1–4 carbons; and
$R_4$ and $R_5$ are hydrogen or lower alkyl of 1–4 carbons; together with pharmaceutically acceptable acid addition salts thereof.

2. The compound of claim 1 in which $R_3$ is hydrogen.
3. The compound of claim 1 in which $R_3$, $R_4$ and $R_5$ are hydrogen.
4. The compound of claim 1 in which $R_1$, $R_3$, $R_4$ and $R_5$ are hydrogen.
5. The compound of claim 1 in which $R_1$, $R_3$, $R_4$ and $R_5$ are hydrogen and $R_2$ is halo.
6. The compound of claim 1 being 6-chloro-7,8-dihydroxy-1-(p-sulfamylphenyl)-2,3,4,5-tetrahydro-1H-3-benzazepine or one of its pharmaceutically acceptable acid addition salts.
7. The compound of claim 1 being 6,9-dichloro-7,8-dihydroxy-1-(p-sulfamylphenyl)-2,3,4,5-tetrahydro-1H-3-benzazepine hydrobromide, hydrochloride or methane sulfonic acid salt.
8. A compound of the formula:

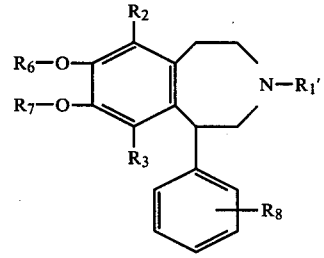

in which:

$R_1'$ is allyl, lower alkyl of 1–4 carbons, trichloroacetyl, benzyloxycarbonyl, trifluoroacetyl or benzyl;
$R_2$ is hydrogen, halo or lower alkyl of 1–4 carbons;
$R_3$ is hydrogen or, when $R_2$ is other than hydrogen, halo or lower alkyl of 1–4 carbons;
$R_6$ and $R_7$ are lower alkyl of 1–4 carbons or, when taken together, methylene or ethylene; and
$R_8$ is $-SO_3H$, $-SO_2Cl$, $-SO_2Br$, $-S-CH_2C_6H_5$ or

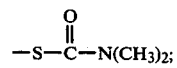

together with acid addition salts thereof acceptable for use as chemical intermediates.

9. The compound of claim 8 in which R₆ and R₇, taken together, are methylene.

10. The compound of claims 8 or 9 in which R₁' is trifluoroacetyl.

11. The compound of claims 8 or 9 in which R₈ is —SO₂Cl.

12. The compound of claim 8 in which R₁' is trifluoroacetyl, R₃ is hydrogen, R₆ and R₇, taken together, are methylene and R₈ is —SO₃H or —SO₂Cl.

13. The compound of claim 8 being 6-chloro-7,8-methylenedioxy-1-(p-sulfophenyl)-2,3,4,5-tetrahydro-1H-3-benzazepine trifluoroacetamide.

14. The compound of claim 8 being 6-chloro-7,8-methylenedioxy-1-(p-chlorosulfonylphenyl)-2,3,4,5-tetrahydro-1H-3-benzazepine trifluoroacetamide.

15. The compound of claim 8 in which R₈ is

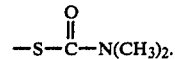

16. The method of including dopaminergic activity in a subject in need thereof comprising administering orally or by injection a nontoxic, dopaminergically effective quantity of the compound of claims 2, 3, 5, 6 or 7.

17. A pharmaceutical composition for inducing dopaminergic activity comprising a nontoxic dopaminergic quantity of the compound of claims 2, 3, 5, 6 or 7 and a dosage unit carrier therefor.

* * * * *

UNITED STATES PATENT AND TRADEMARK OFFICE
CERTIFICATE OF CORRECTION

PATENT NO. : 4,285,938

DATED : August 25, 1981

INVENTOR(S) : Francis R. Pfeiffer

It is certified that error appears in the above—identified patent and that said Letters Patent is hereby corrected as shown below:

Column 20, line 7, change -- including -- to -- inducing -- .

Signed and Sealed this

First Day of December 1981

[SEAL]

Attest:

GERALD J. MOSSINGHOFF

Attesting Officer    Commissioner of Patents and Trademarks